United States Patent
Bon et al.

(10) Patent No.: US 6,695,772 B1
(45) Date of Patent: Feb. 24, 2004

(54) SMALL DIAMETER CANNULA DEVICES, SYSTEMS AND METHODS

(75) Inventors: Ed Bon, Canton, GA (US); Bart Bracy, Naples, FL (US)

(73) Assignee: Visionary Biomedical, Inc., Roswell, GA (US)

( * ) Notice: Subject to any disclaimer, the term of this patent is extended or adjusted under 35 U.S.C. 154(b) by 51 days.

(21) Appl. No.: 10/125,132

(22) Filed: Apr. 17, 2002

Related U.S. Application Data (63) Continuation-in-part of application No. 10/109,202, filed on Mar. 28, 2002, and a continuation-in-part of application No. 09/995,039, filed on Nov. 26, 2001.

(51) Int. Cl.⁷ .................................................. A61B 1/04
(52) U.S. Cl. .................... 600/114; 600/125; 605/164.01
(58) Field of Search .................................. 600/114, 120, 600/121, 125; 604/164.01, 264

(56) References Cited

U.S. PATENT DOCUMENTS

| | | |
|---|---|---|
| 3,822,697 A | 7/1974 | Komiya |
| 4,253,467 A | 3/1981 | Frazier |
| 4,254,762 A * | 3/1981 | Yoon .......................... 600/114 |
| 4,345,589 A | 8/1982 | Hiltebrandt |
| 4,550,715 A | 11/1985 | Santangelo et al. |
| 4,610,242 A | 9/1986 | Santangelo et al. |
| 4,685,450 A | 8/1987 | Collins et al. |
| 4,688,554 A | 8/1987 | Habib |
| 4,696,544 A * | 9/1987 | Costella ....................... 385/118 |
| 4,740,058 A | 4/1988 | Hori et al. |
| 4,765,314 A | 8/1988 | Kolditz et al. |
| 4,784,117 A * | 11/1988 | Miyazaki .................... 600/114 |
| 4,807,594 A | 2/1989 | Chatenever |
| 4,844,071 A | 7/1989 | Chen et al. |
| 4,959,058 A | 9/1990 | Michelson |
| 4,972,827 A | 11/1990 | Kishi et al. |
| 4,973,321 A | 11/1990 | Michelson |
| 5,127,393 A | 7/1992 | McFarlin et al. |
| 5,188,093 A | 2/1993 | Lafferty et al. |
| 5,323,767 A | 6/1994 | Lafferty et al. |
| 5,329,936 A | 7/1994 | Lafferty et al. |
| 5,351,678 A | 10/1994 | Clayton et al. |
| 5,359,992 A | 11/1994 | Hori et al. |
| 5,456,673 A * | 10/1995 | Ziegler et al. .............. 604/264 |
| 5,526,820 A | 6/1996 | Khoury |
| 5,571,147 A | 11/1996 | Sluijter et al. |
| 5,620,408 A | 4/1997 | Vennes et al. |
| 5,662,680 A | 9/1997 | Desai |
| 5,695,448 A | 12/1997 | Kimura et al. |

(List continued on next page.)

OTHER PUBLICATIONS www.acueity.com/pages/products2/html.
Citation Medical Corporation Brochure Citscope™ 16 Model No. 1621, 2 pages (09/91).

(List continued on next page.)

*Primary Examiner*—Roy D. Gibson
(74) *Attorney, Agent, or Firm*—Geoffrey K. Gavin; Dean W. Russell; Kilpatrick Stockton LLP

(57) ABSTRACT

The present invention relates to devices, systems, and methods for obtaining a quick diagnostic view of a cavity or joint of a patient and/or delivering a therapeutic treatment to that cavity or joint. The invention relates specifically to a cannula device that is sized for insertion into a patient for diagnosis or treatment in an office-based procedure and that has a securing mechanism that allows a scope or other instrument to be adjusted with respect to the cannula. Various optional features of the invention include a rotatable sleeve and an adapter for changing the working length of the cannula. The invention also relates to methods for performing an office-based diagnostic procedure and to kits for assisting the performance of such procedures.

32 Claims, 4 Drawing Sheets

U.S. PATENT DOCUMENTS

| | | |
|---|---|---|
| 5,779,624 A | 7/1998 | Chang |
| 5,792,044 A | 8/1998 | Foley et al. |
| 5,807,237 A | 9/1998 | Tindel |
| 5,836,867 A | 11/1998 | Speier et al. |
| 5,846,182 A | 12/1998 | Wolcott |
| 5,868,665 A | 2/1999 | Biggs |
| 5,897,269 A | 4/1999 | Ross et al. |
| 5,902,231 A | 5/1999 | Foley et al. |
| 5,941,815 A | 8/1999 | Chang |
| 5,954,635 A | 9/1999 | Foley et al. |
| 5,961,445 A | 10/1999 | Chikama |
| 5,976,075 A | 11/1999 | Beane et al. |
| 5,980,450 A | 11/1999 | Thompson |
| 6,030,360 A | 2/2000 | Biggs |
| 6,110,103 A | 8/2000 | Donofrio |
| 6,113,533 A | 9/2000 | Howes et al. |
| 6,120,434 A | 9/2000 | Kimura et al. |
| 6,126,591 A | 10/2000 | McGarry et al. |
| 6,146,355 A | 11/2000 | Biggs |
| 6,152,871 A | 11/2000 | Foley et al. |
| 6,176,823 B1 | 1/2001 | Foley et al. |
| 6,196,967 B1 * | 3/2001 | Lim et al. .................. 600/125 |
| 6,206,822 B1 | 3/2001 | Foley et al. |
| 6,213,974 B1 | 4/2001 | Smith et al. |
| 6,217,509 B1 | 4/2001 | Foley et al. |
| 6,234,958 B1 | 5/2001 | Snoke et al. |
| 6,261,311 B1 | 7/2001 | Sharkey et al. |
| 6,264,651 B1 | 7/2001 | Underwood et al. |
| 6,419,654 B1 * | 7/2002 | Kadan ........................ 604/27 |
| 2001/0018500 A1 | 8/2001 | Boebel et al. |
| 2001/0025134 A1 | 9/2001 | Bon et al. |
| 2002/0019591 A1 | 2/2002 | Bon |

OTHER PUBLICATIONS

Citation Medical Corporation Brochure entitled Definitive Arthroscopy At Your Disposal. Introducing Citscope™ The First Disposable Arthroscope. 10 pages (1991).

* cited by examiner

SMALL DIAMETER CANNULA DEVICES, SYSTEMS AND METHODS

This application is a continuation in part to application Ser. No. 09/995,039, filed Nov. 26, 2001, titled "Delivery Devices, Systems, and Methods," and a continuation in part of application Ser. No. 10/109,202, filed Mar. 28, 2002, titled "Apparatus and System for Connecting Medical Instruments and Devices," the entire contents of each of which are hereby incorporated by reference.

BACKGROUND OF INVENTION

1. Field of Invention

This invention relates to small diameter cannula devices, systems and methods for use in conjunction with a fiberoptic scope or other instrument for use that allows a medical practitioner to visualize a particular surgical site, to introduce or remove fluids from the site, or to deliver a therapeutic treatment to the site. The cannula device has a diameter that is small enough to allow it to be used in a medical practitioner's office for a quick diagnosis or treatment without requiring operating room time.

2. Description of Related Art

The use of fiberoptic scopes for viewing a surgical site is common practice. For example, during arthroscopic surgery, an arthroscope is introduced into a knee, shoulder, hip, or other joint. Generally, the arthroscope is attached to a camera head, a remote light source and a video monitor and inserted into a synovial joint (e.g., knee, shoulder, etc.) through a small portal incision in the overlying skin and joint capsule. Surgical instruments may be placed in the joint through similar portal incisions, with their use being guided by arthroscopic visualization. Throughout the procedure, physiologic irrigation fluid (e.g., normal saline or lactated Ringer's) is flushed intermittently or continuously through the joint, distending the joint capsule and removing debris, thereby improving intra-articular visualization. Although irrigation liquid is typically used, it is also possible to use gas or other distension media to distend the space. As a result of widening surgical indications and the development of small diameter arthroscopes, wrist and ankle arthroscopies also have become routine.

During endoscopic surgery, endoscopes are commonly inserted into a patient through a cannula. Generally, cannulas are thin hollow tubes that, among other things, provide a tunnel between the cavity to be viewed and the outside of the patient's body, allow rapid exchange of various endoscopes and instruments during the procedure if necessary, protect the lens at the end of the endoscope, keep soft tissue away from the endoscope, and maintain the fluid or air content of the cavity, joint or potential space. The cannula commonly stays in place for the duration of the procedure. An endoscope may be housed entirely within the cannula (for use as a traditional, rigid endoscope) or may extend from the tip of the cannula so that movement of a flexible tip is possible.

Generally, during the use of such cannulas, a trocar, which is a rigid instrument having a sharpened tip, and/or a blunt obturator, is inserted through the cannula and projects a short distance from the end of the cannula for forming a small puncture wound in the patient's skin. This provides a route for the insertion of the cannula. The trocar is then removed, leaving the cannula in position with its distal end located in a desired position and its proximal end extending outside the patient. Various instruments may then be inserted through the cannula, such as cutting instruments, viewing instruments, irrigation tubes, and the like.

For example, some endoscope insertion cannulas have an increased diameter on the proximal end to accommodate a locking mechanism. These cannulas typically lock an endoscopy instrument in a desired position with a spring and pin-type locking mechanism. Cannulas may also have an irrigation port through which irrigation and aspiration can be introduced down the cannula tube. There are also cannulas for use in conjunction with endoscopes that are adapted to extend and retract, or to telescopically slide into various positions, based upon the desired use. Other cannulas are particularly adapted for use at locations deep within the body. Such cannulas generally have a working channel that is configured to simultaneously accept a plurality of movable instruments.

Additional introducers for various medical instruments are also available. For example, there are provided rigid tubular introducers having an internal lumen of a uniform diameter. The wall thickness of the most distal portion (the portion closest to the surgical site) varies between 0.019 inch and 0.005 inch. A Tuohy-Borst type clamp at the end of the introducer maintains the endoscope in place.

There are also endoscope sheaths which enable irrigating fluid to flush surgical debris away from the viewing end of an endoscope without contacting the endoscope itself. Such sheaths have an end cap at the end of the sheath to shield the endoscope from the surgical environment. Such sheaths also have channels to prevent communication between the endoscope and the receiving space within the sheath.

However, arthroscopic and endoscopic surgery are involved surgeries that take place under general or local anesthesia in an operating room. On the other hand, often times a practitioner may simply wish to view a particular site within the patient without actually performing surgery. For example, a surgeon may take an x-ray image of a joint and wish to see whether the tissue surrounding the joint is inflamed or irritated prior to performing surgery, or may wish to examine a surgical site post-surgery. Additionally or alternatively, a surgeon may wish to drain or irrigate a joint or deliver a therapeutic treatment to a joint, while being able to visualize the surrounding area. Optimally, in the interest of a rapid diagnosis and the least inconvenience to the patient, it is desirable for such a minimally invasive, diagnostic procedure to be performed in the practitioner's office rather than scheduling operating room time or subjecting the patient to multiple procedures and/or appointments.

Although the medical device industry has attempted to manufacture cannula systems for in-office diagnosis, these systems have not been successful. Among other reasons, this is in part due to the poor image quality generated by the disposable scopes used and in part due to the lack of adjustability of the scope once it is placed in the sheath.

For example, there are disposable arthroscopes which generally have a 1.6 mm outer diameter and are used in conjunction with a 2.1 mm sheath. The sheath has one in-flow tube that is fixed in place on the sheath. The system is intended for office-based arthroscopy.

The connection between the sheath and the scope in this system is fixed. Once the scope is inserted into the sheath and locked into place, there is no option or mechanism that allows the scope to be moved. In other words, if the scope extends slightly from the end of the sheath, there is no way for the surgeon to maneuver the scope so that it extends further from the sheath, retracts slightly into the sheath or lies flush with the end of the sheath. The surgeon cannot compensate for slight differences in manufacturing tolerances between the scope and the sheath. Whatever view is provided in the locked position determines the surgeon's view. Moreover, in the case of flexible fiberoptic scopes, if the scope needs to be removed and replaced, there is no locking mechanism that allows the surgeon to return the scope to its original orientation and position.

Additionally, after the procedure has been performed, the scope is disposed. It has been found, however, that lower end, disposable scopes do not offer a high resolution scope or a quality image.

Accordingly, one feature of the present invention is that it provides devices and methods that allow such diagnostic procedures to be conducted in a practitioner's office, while providing a clear image and secure positioning, but maneuverability and adjustability, of the scope.

Another feature of the present invention is that it provides an ergonomic handle and at least one rotatable luer port for ease of use.

A further feature of this invention is that it provides a connection mechanism for attachment of a scope that allows adjustability of the scope during use.

Another feature of this invention is that it provides methods for conducting an in-office diagnostic procedure that is quick and relatively painless to the patient, while providing the surgeon with a clear view and maneuverability of the scope in use.

An additional feature of this invention is that it provides a high-quality fiberoptic scope that can be adjusted during use, and particularly, removed and then replaced in the original orientation, and that is adapted to be re-used.

Another feature of the present invention is that it provides a surgical diagnostic method that can be performed without incurring great expense and without requiring general anesthesia or actual operating room time.

SUMMARY OF INVENTION

The present invention provides devices, systems, and methods for obtaining a quick diagnostic view of a cavity or joint of a patient and/or delivering a therapeutic treatment to that cavity or joint. Devices according to the preferred embodiment of the invention provide high quality images because the small cannula devices are particularly adapted for use with a flexible fiberoptic scope that can be adjusted with respect to the cannula device.

A particular embodiment of the invention comprises a small diameter cannula device having a hollow tube adapted to receive an instrument, such as a fiberoptic scope, and sized for insertion into a patient for diagnosis or treatment in an office-based procedure. (As used herein, the terms "office-based" or "in-office" procedure means a procedure that can be performed without operating room personnel and equipment due to the minimally invasive techniques provided herein and the lack of general anesthesia or an epidural typically required for arthroscopic surgery. However, it is possible to use the current devices, systems and methods in an operating room, in a sports locker-room, on-site by paramedics, and so forth.)

The hollow tube extends from a main body which has a securing mechanism at the other end of the main body in communication with the hollow tube. The securing mechanism is adapted to receive and lock an instrument in place (in most instances, the instrument will be a fiberoptic scope, but may alternatively be a cutting instrument or other mechanical device or an energy delivery device (RF, laser, UV, and so forth). The securing mechanism also allows for at least some adjustment of the instrument such that the instrument can be adjusted to protrude from the distal end, be flush with the distal end, be retracted from the distal end into the hollow tube, and combinations thereof, while the instrument remains locked in place.

In a more specific embodiment, the main body has at least one rotatable sleeve having a connection port in communication with the hollow tube for delivering or excavating fluids or delivering therapeutic agents to a surgical site.

Further embodiments provide a rotatable sleeve with a connection port that is rotatable independent from the main body in order to prevent tubing from wrapping around the main body as the main body is manipulated. In a more particular embodiment, the connection port comprises two female luer connectors.

In an alternate embodiment, the hollow tube is surrounded by a main body that has at least one finger tang.

In a further embodiment of the invention, the device includes an adapter for changing the working length of the hollow tube allowing the cannula device to be used for both small and large joints. Specifically, the adapter may protrude from the end of the main body from which the hollow tube protrudes for shortening the insertable portion of the hollow tube and for adapting the cannula device for use in small joint procedures.

A further embodiment of the invention provides a securing mechanism for retaining an instrument in place that is adapted to allow the instrument, such as a fiberoptic scope, to be positioned within the hollow tube upon initial insertion and then repeatedly removed and reinserted without readjusting the position of the instrument or removing the cannula device to reposition the instrument. In a particular embodiment, the securing mechanism comprises an apparatus for connecting an instrument to the cannula, wherein the instrument may be at least partially inserted within the cannula, comprising (a) a linear translation mechanism for adjusting the instrument along a longitudinal axis of the cannula to a position and (b) a locking mechanism for retaining the instrument in an orientation upon initial insertion of the instrument within the cannula and adapted to allow the instrument to be removed and reinserted without readjusting the orientation or the position of the instrument or moving the cannula to reposition the instrument.

In a further embodiment, the securing mechanism comprises a main body with at least one alignment slot; an adapter body that fits at least partially within the main body and including at least one post adapted to fit in the at least one alignment slot and a j-hook slot adapted to receive a protrusion of the instrument; and a rotatable collar with at least one adjustment slot adapted to receive the at least one post, wherein the rotatable collar fits over the main body and the adapter body.

In another embodiment, the cannula device is a single-use, disposable device. In a particular embodiment, the device comprises molded plastic.

In another embodiment, the cannula device is a reusable device.

Other embodiments of the invention provide 0-ring seals at the docking port and connection port adapted to prevent fluids from passing from the cannula device to the environment.

Further embodiments include the use of the cannula system with a fiberoptic scope, a trocar, and/or a blunt obturator to assist entry of the cannula into a patient.

In use, a particular method for performing a diagnostic procedure includes providing at least one small diameter cannula device of the type described above, creating an entry path in order to deliver the cannula device to the desired surgical site, inserting the cannula device through the entry path, inserting a fiberoptic scope and securing the scope in place with the securing mechanism, and viewing the site. Specifically, the surgeon may desire to use a trocar and/or an obturator and/or make a small incision to facilitate the insertion of the cannula device. It is also possible to insert an instrument other than a scope into the cannula and/or apply an irrigation or suction tube to the connection port in order to irrigate or suction the site or to deliver a therapeutic treatment to the site. Further, an adapter may be attached to an end of the main body to shorten the insertable portion of the hollow tube and for adapting the cannula device for use with small joints.

Further embodiments of the invention provide kits for performing the methods described above.

These and other objects, features, and advantages of the present invention may be more clearly understood and appreciated from a review of the following detailed description of some exemplary embodiments and by reference to the appended drawings.

DETAILED DESCRIPTION

This invention will now be described more fully with reference to the drawings, showing preferred embodiments of the invention. However, this invention can be embodied in many different forms and should not be construed as limited to the embodiments set forth.

Figure 1:
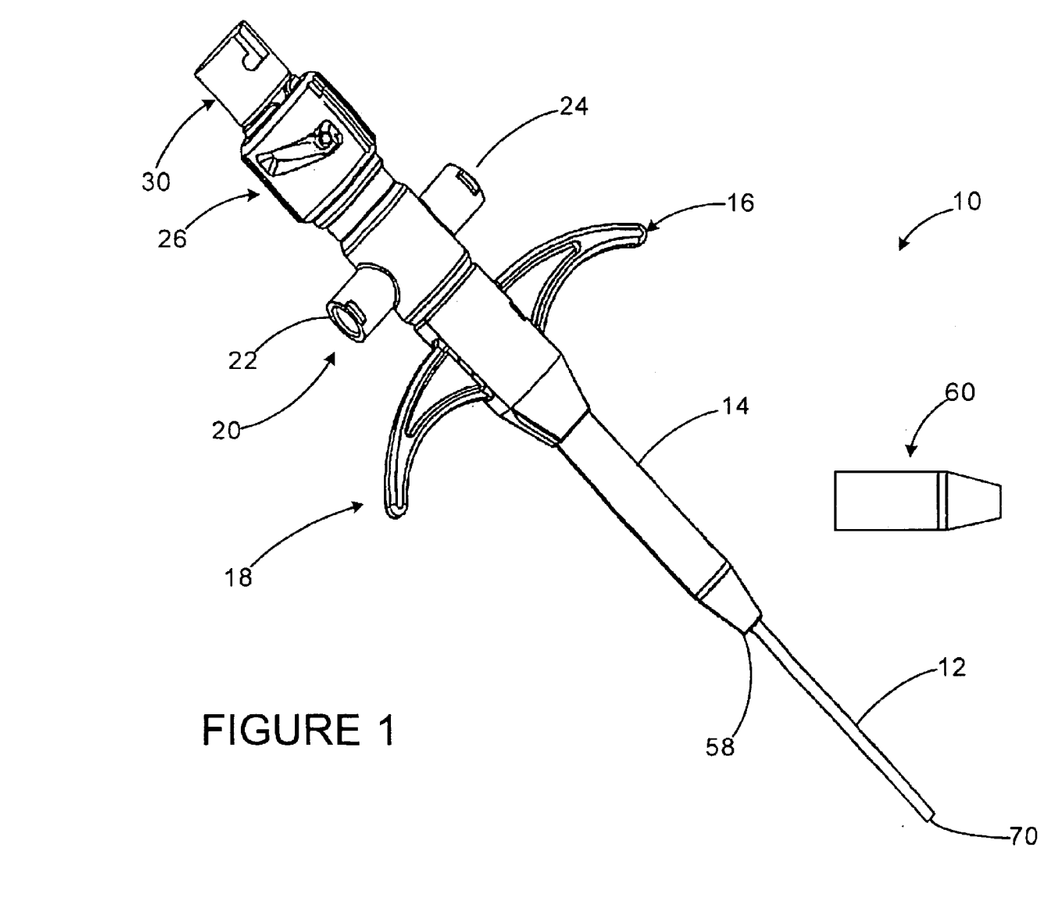
FIG. 1 shows a small diameter cannula according to one embodiment of the present invention.

As shown in FIG. 1, the present invention provides a cannula device 10 having a hollow tube 12 and a main body 14. Hollow tube 12 is sized for insertion into a patient for diagnosis or treatment during an office-based procedure. In a particular embodiment, it is about the same size as a 14 gauge needle. Generally, the cannula device 10 mimics a needle or tube 12 that can be inserted into a patient without an epidural or general anesthesia. It may be desired to use local or topical anesthesia to ease a patient's anxiety or pain from the initial insertion, but the small size of tube 12 alleviates the need for a full operating room set-up. Hollow tube 12 is adapted to be positioned at or near a surgical site and to receive and deliver an instrument, which includes but is not limited to a fiberoptic scope, a cutting instrument, and/or an energy delivery device (such as RF, laser, UV), or other therapeutic treatment, such as irrigation, suction, and/or delivery of fluids or drugs that are required for a particular site. By way of non-limiting example, fluids that may be delivered using this invention include steroids, anti-inflammatory agents, and the like.

In the particular embodiment shown, main body 14 of device 10 has finger tangs 16 and 18. Providing one or more finger tangs allows the practitioner a greater degree of control over the placement of hollow tube 12, as well as provides enhanced stabilization of device 10 in use.

Proximal of finger tangs 16 and 18 is rotatable sleeve 20. In a particular embodiment, main body 14 has one rotatable sleeve 20 which in turn, has two luer connectors 22 and 24. However, more than one rotatable sleeve and more or less luer connectors are considered within the scope of this invention.

Luer connectors 22 and 24 allow the connection of tubing from an irrigation source, a suction source, or the like for introduction or excavation of fluids from the patient. Because rotatable sleeve 20 is independently rotatable about the main body 14, main body 14 can be maneuvered without the attached tubing wrapping around main body 14 as device 10 is manipulated. Although this feature is not required and a non-rotatable sleeve is within the scope of this invention, rotatable sleeve 20 is preferred because it enhances the ease of use of cannula device 10.

Although luer connectors 22 and 24 are shown directly attached to rotatable sleeve 20, one skilled in the art would understand that tubing could extend from rotatable sleeve 20 and luer connectors 22 and 24 could be located at the ends of the tubing. Providing luer connectors 22 and 24 attached to main body 14 allows luer connectors 22 and 24 to be easily capped when not in use and prevents excess tubing from interfering with the practitioner's surgical field.

Toward the proximal end 26 of main body 14 is securing mechanism 30. Securing mechanism 30 is adapted to receive and lock an instrument, such as a fiberoptic scope, in place while also providing for at least some adjustment of the instrument. A particular embodiment of securing mechanism 30 is shown and described, but it is understood that any mechanism that can retain an instrument while providing adjustment features is considered within the scope of this invention.

In a particular embodiment, the securing mechanism 30 allows a scope or other instrument, once inserted, to be adjusted. A practitioner may wish to have the scope slightly protrude from distal end 70 of hollow tube 12, be flush with distal end 70, be retracted from distal end 70 so that the tip of the scope or other instrument remains in hollow tube 12, and combinations thereof, all while the scope (or whatever instrument is being used) remains locked in place. For example, among other reasons, it may be necessary to move a scope while it is in place in the cannula device 10 in order to protect the scope from abrading certain tissue, to enhance the practitioner's view of the site, to adjust for any angle that may be provided on the scope if applicable.

Additionally, securing mechanism 30 allows the fiberoptic scope or other instrument to be positioned within cannula device 10 upon initial insertion, and then repeatedly removed and reinserted into cannula device 10 without readjusting its position or removing the cannula device 10 to reposition.

Figure 4:
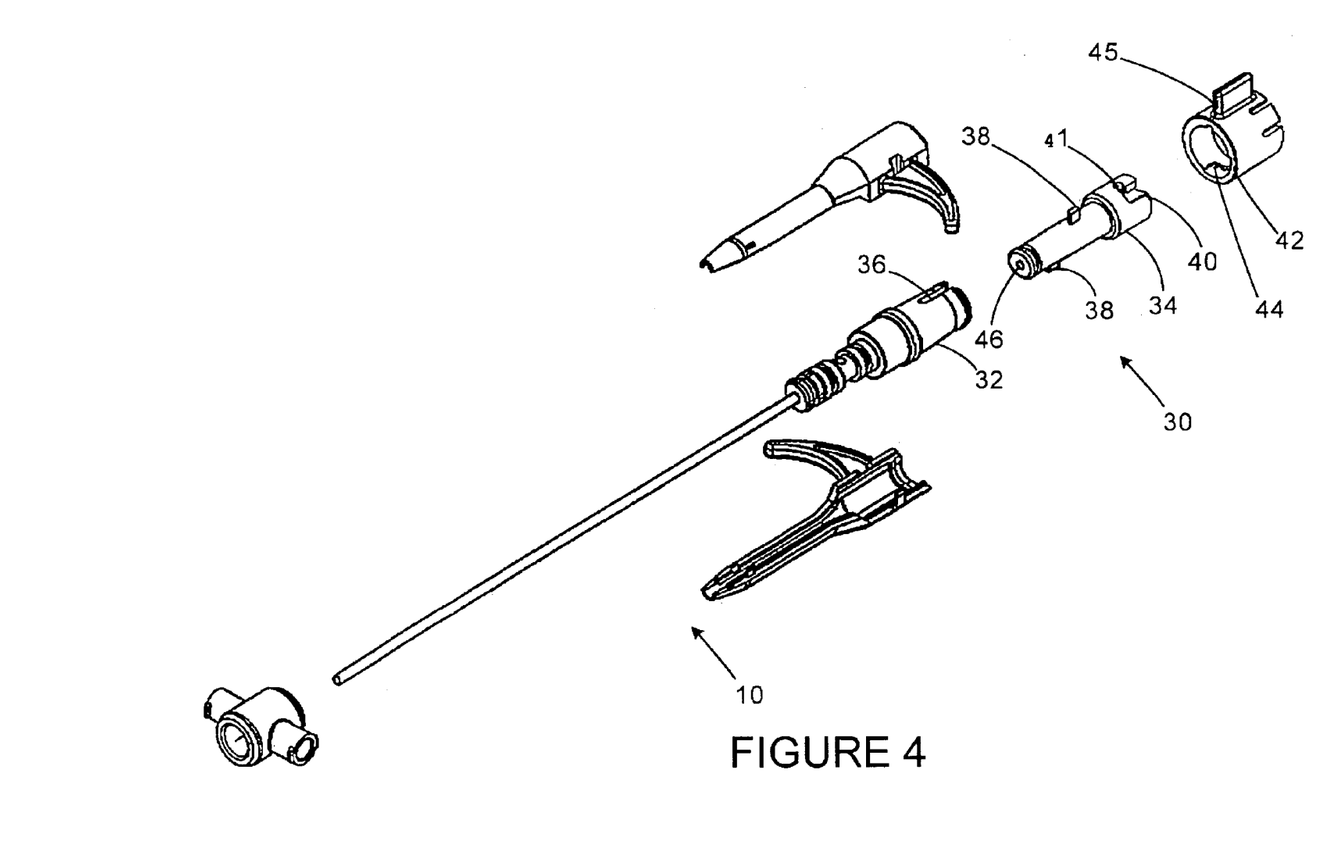
FIG. 4 shows a securing mechanism according to one embodiment of the invention.

The exemplary securing mechanism 30 shown in FIG. 4 has a core body 32, an adapter body 34, and a rotatable collar 42. Optionally, core body 32 may be permanently attached to the cannula device 10, as shown in FIG. 4. Core body 32 includes at least one alignment slot 36. In a particular embodiment, main body 32 includes two alignment slots 36 located approximately 1800 from each other. Those skilled in the art understand that any number of alignment slots may be used and that the location of the alignment slots may vary.

Adapter body 34 includes a locking mechanism. As shown in FIG. 4, the locking mechanism includes at least one j-hook slot 40 that may be used to secure an instrument, such as a fiberoptic scope to securing mechanism 30. A pin or other protrusion on an instrument (not shown) works in conjunction with j-hook slot 40 to secure the instrument. The instrument is inserted into securing mechanism 30 with the pin aligned with j-hook slot 40. The pin slips into j-hook slot 40, and the instrument is rotated such that the pin fits into a lower horizontal portion 41 of j-hook slot 40. Thus, j-hook slot 40 allows a user to lock or unlock the instrument by simply rotating the instrument. Once the instrument is secured, there is no rotation of the instrument itself. This is significant, for example, when the instrument is a scope because securing the instrument's orientation maintains the orientation of the visual image provided by the scope and prevents the orientation of the visual image from being inadvertently changed.

The instrument is typically of a length corresponding substantially to the cannula device 10 to which the instrument is being connected, such that the end of the instrument fits snugly against the securing mechanism and, with fine tuning, the instrument protrudes from, is flush with, or is recessed within the device 10, as desired. However, an instrument that is too long to both fit snugly against the connector and be in a desirable position may still be utilized by using an adaptive coupler with a pin or protrusion located thereon. Such an adaptive coupler may be clamped to the instrument. In this way, an instrument that it is too long may be locked in position by the locking mechanism of the present invention. For a more detailed explanation of an exemplary securing mechanism, see U.S. application Ser. No. 10/109,202, filed Mar. 28, 2002, titled "Apparatus and System for Connecting Medical Instruments and Devices," the entire contents of which are hereby incorporated by reference.

In a more particular embodiment, the cannula device 10 includes adapter 60. Adapter 60 is shown in FIG. 1 having a bullet-type shape, but any adapter that can change the working length of hollow tube 12 to allow cannula device 10 to be used for both small and large joints is considered within the scope of this invention. Working length is defined as the insertable portion of the hollow tube 12. In the embodiment shown, adapter 60 is attached to end 58 of main body 14. By extending the length of main body 14, the length of hollow tube 12 that remains available for insertion decreases. Thus, in this embodiment, adapter 60 converts cannula device 10 for use with smaller joints.

Although not shown, alternatively, hollow tube 12 could be detachable from main body 14 and an extended portion of hollow tube could be attached to end of main body 14, acting as an adapter. In this embodiment, the adapter lengthens the portion of hollow tube that remains available for insertion into a patient. In other words, an extended portion of hollow tube could also be considered an adapter. This embodiment, however, would most likely require that the length of the scopes and instruments change, and is therefore not as preferable as the embodiment shown using adapter 60.

In a preferred embodiment, O-ring seals are employed throughout cannula device 10 to ensure that fluids cannot pass from the internal cavities of cannula device 10 through any joints to the environment. For example, it is preferred that there be an Oring connection at or near securing mechanism 30.

Additionally, cannula device 10 is preferably a single-use, disposable device that is, for example, made of molded plastic. Alternatively, cannula device 10 may be a sterilizable item, for example, made from stainless steel. It is preferable, however, that cannula device 10 be disposable, which alleviates sterilization concerns, allows the device to be manufactured more cost-effectively, and enhances ease of use.

It is also preferable that cannula device 10 be used in conjunction with a high quality, reusable scope, such as certain proprietary scopes manufactured and provided by Visionary BioMedical, Inc. Although disposable scopes may be used and are considered within the scope of this invention, reusable scopes have been found to provide higher quality images.

The present invention also provides systems and methods for obtaining a quick diagnostic view of a cavity or joint of a patient and/or delivering a therapeutic treatment to that cavity or joint. There are provided methods for insertion of the device and methods for using device for visualization of a surgical site.

Figure 3:
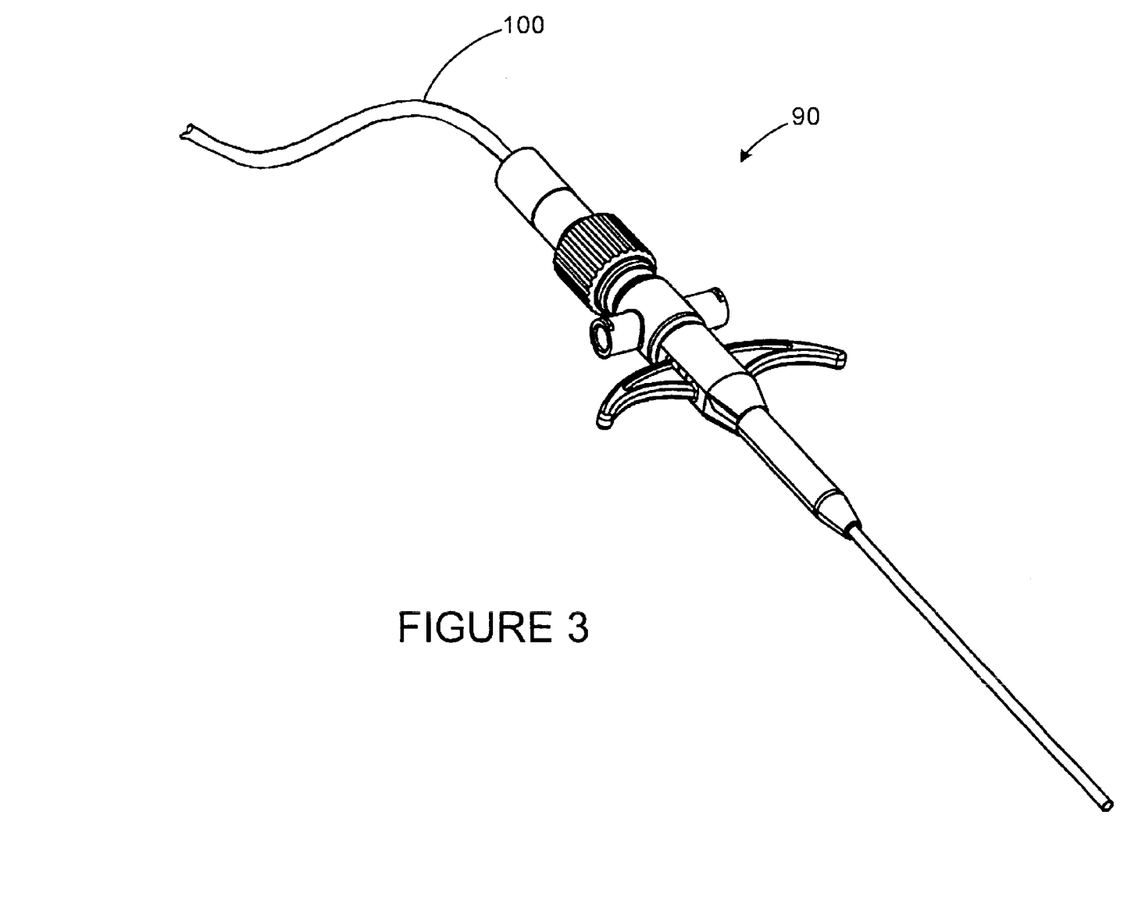
FIG. 3 shows a further embodiment of a small diameter cannula having a scope connected thereto.

In practice, the scope is traditionally first inserted into the cannula and adjusted using the securing mechanism 30 so that proper viewing can be attained through distal tip 70 of cannula device 10. Specifically, the scope is introduced into the sterile field and connected to a camera head and light cable (not shown). The scope is then inserted into the cannula device 10 and locked into position by first aligning and then engaging the a pin or other protrusion or post (not shown) on the scope into the adapter body 34 and turning the scope until it locks into position. The rotatable collar 42 is then rotated until the tip of the scope is flush with the end 70 of cannula device 10. Although not required, it is preferable to adjust the camera by powering the video system and performing a white balance procedure, as in known in the art. The scope is then removed from the cannula device and the cannula device is prepared for insertion. In general, this practice ensures that the scope is properly focused and oriented.

Figure 2:
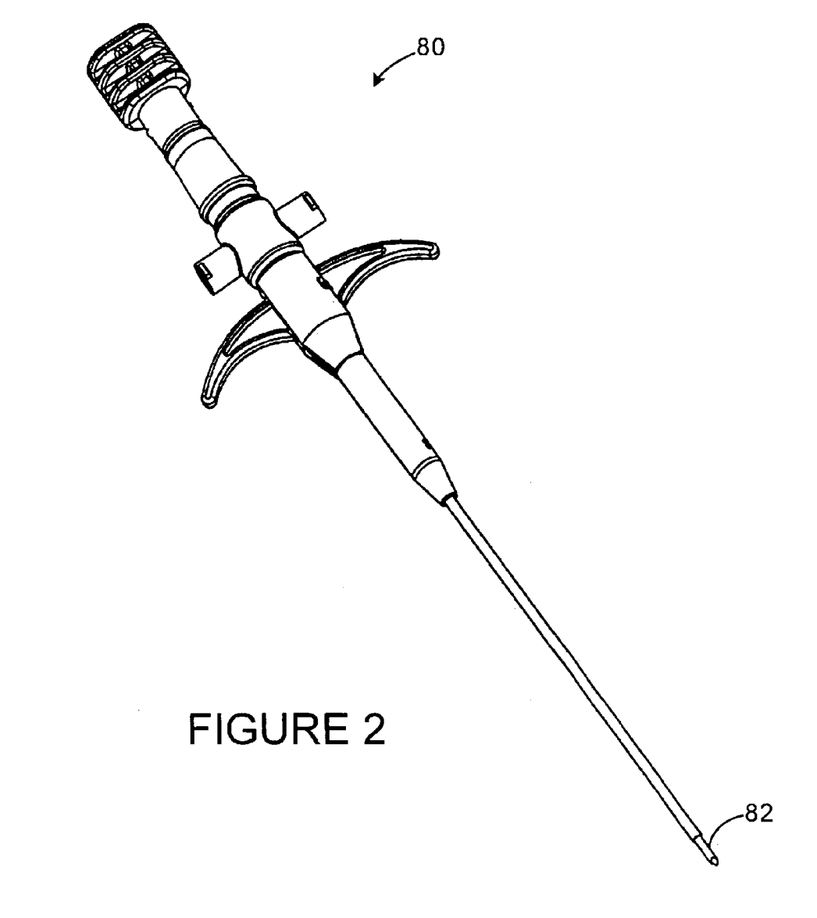
FIG. 2 shows an alternate embodiment of a small diameter cannula having a trocar placed therein.

In order to place cannula device 10 at the desired surgical site, a needle, preferably a 16 gauge needle, is placed into the desired entry path into the site to be examined. A synovial fluid biopsy can be taken and/or sterile saline, gas, or other distension media, may be injected into the site to distend the space. After the needle is removed, in a first embodiment, a trocar 82 is placed into the cannula device 10 to assist placement of the device. The cannula and trocar assembly is advanced through tissue layers to the joint capsule (or other site to be examined), following the path created by the 16 gauge needle. The trocar is then removed.

In another embodiment, after the needle is removed, a small skin incision is made to accommodate the insertion of the cannula device 10 without the use of a trocar.

In both embodiments, however, it is preferred that a blunt obturator (not shown) then be inserted into the cannula device and that the obturator and cannula device assembly be advanced further to the surgical site, such as through tissue layers, through the capsule, and into the joint space (or other surgical site) to be examined. Specifically, when the surgical site is a synovial joint, the obturator and cannula are advanced down to the joint capsule. The use of an obturator is intended to minimize potential damage to delicate tissue surfaces that might occur from contact with the trocar. After the obturator is removed, a scope or other instrument is inserted and locked into place by a securing mechanism.

If necessary, tubing (not shown) is then attached to one or both luer connectors 22 and 24 to allow infusion of fluids for improved visualization and to distend or lavage the cavity. Gas or other distension media may also be delivered. Fluid can also be extracted from the cavity via suction from one of the luer connectors 22 and 24. The surgeon may also apply irrigation and suction intermittently to help provide a clear image to enable a thorough examination of the joint or other surgical site.

Additionally or alternatively, during the procedure, the surgeon may wish to deliver a therapeutic treatment, including but not limited to a steroid, a visco-supplement, or a dye to assist imaging of the joint or cavity, and so forth. Such treatments can be delivered through luer connectors 22 and 24 or the scope may be removed and the treatment may be delivered directly through main body 14 through hollow tube 12.

Due to the features of securing mechanism 30, the scope can be removed at any time during the procedure for various purposes, for example, to clean the lens, and be reinserted in the same position as long as the securing mechanism 30 has not been moved from its original position.

If the practitioner wishes to use the device on a joint that is smaller or larger than the working length of hollow tube, an adapter may be used, such as adapter 60.

The present invention also relates to kits for performing the diagnostic procedures described herein and kits having the elements and features described herein may be provided. For example, one embodiment of this invention comprises a kit having at least one small diameter cannula device, an adapter for changing the working length of the cannula, a fiberoptic scope, a trocar, and a blunt obturator to assist entry of the cannula. More specifically, the kit may also be provided with tubing for connection to irrigation or suction sources, bandages for application to the wound site, gauze pads, alcohol swabs, surgical drapes, and so forth.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A small diameter cannula device, comprising:
    (a) a hollow tube adapted to receive an instrument having the size of a fiberoptic scope, the tube having a distal end sized for insertion into a patient for diagnosis or treatment during an office-based procedure;
    (b) a main body having an end from which the hollow tube protrudes; and
    (c) a securing mechanism toward a proximal end of the main body and in communication with the hollow tube, the securing mechanism adapted to receive and lock the instrument in place while also providing for at least some adjustment of the instrument such that the instrument can be adjusted to protrude from the distal end, be flush with the distal end, be retracted from the distal end into the hollow tube, and combinations thereof, while the instrument remains locked in place.

2. The small diameter cannula device of claim 1, wherein the main body further comprises at least one rotatable sleeve having a connection port in communication with the hollow tube for delivering or excavating fluids or delivering therapeutic agents to a surgical site.

3. The small diameter cannula device of claim 2, wherein the rotatable sleeve having a connection port is rotatable independent from the main body in order to prevent tubing from wrapping around the main body as the main body is manipulated.

4. The small diameter cannula device of claim 2, wherein the connection port comprises two female luer connectors.

5. The small diameter cannula device of claim 1, wherein the main body has at least one finger tang.

6. The small diameter cannula device of claim 1, wherein the hollow tube is about the same size as a 14-gauge needle.

7. The small diameter cannula device of claim 1, wherein the securing mechanism for retaining the fiberoptic scope in place is adapted to allow the fiberoptic scope to be positioned within the hollow tube upon initial insertion and then repeatedly removed and reinserted without readjusting the position of the scope or removing the cannula device to reposition the scope.

8. The small diameter cannula device of claim 7, wherein the securing mechanism comprises an apparatus for connecting an instrument to the cannula, where in the instrument may be at least partially inserted within the cannula, comprising
    (a) a linear translation mechanism for adjusting the instrument along a longitudinal axis of the cannula to a position; and
    (b) a locking mechanism for retaining the instrument in an orientation upon initial insertion of the instrument within the cannula and adapted to allow the instrument to be removed and reinserted without readjusting the orientation or the position of the instrument or moving the cannula to reposition the instrument.

9. The small diameter cannula device of claim 8, wherein the locking mechanism comprises a j-hook slot in an adapter body that fits at least partially within a core body and is secured within the core body by a rotatable collar.

10. The apparatus of claim 9, wherein the j-hook slot is adapted to receive a protrusion of the scope.

11. The apparatus of claim 7, wherein the linear translation mechanism comprises a rotatable collar with at least one adjustment slot.

12. The apparatus of claim 11, wherein the at least one adjustment slot is adapted to receive a corresponding post of an adapter body such that when the rotatable collar is rotated, the scope is caused to move along the longitudinal axis of the cannula without affecting the orientation of the scope.

13. The small diameter cannula device of claim 1, wherein the cannula device is a single-use, disposable device.

14. The small diameter cannula device of claim 1, wherein the cannula device comprises molded plastic and a metal tube.

15. The small diameter cannula device of claim 1, wherein the cannula device is a reusable device.

16. The small diameter cannula device of claim 1, wherein the main body has a series of O-ring seals at the docking port and connection port adapted to prevent fluids from passing from the cannula device to the environment.

17. The small diameter cannula device of claim 1, further comprising a fiberoptic scope adapted to be used with the cannula device.

18. The small diameter cannula device of claim 1, further comprising a trocar, a blunt obturator, or both, for use with the cannula device to assist entry of the cannula device into a patient.

19. The small diameter cannula device of claim 1, wherein the instrument instrument having the size of a fiberoptic scope is a fiberoptic scope.

20. A small diameter cannula device, comprising:
    (a) a hollow tube adapted to receive an instrument having the size of a fiberoptic scope, the tube having a distal end sized for insertion into a patient for diagnosis or treatment during an office-based procedure;
    (b) a main body having an end from which the hollow tube protrudes;
    (c) a securing mechanism toward a proximal end of the main body and in communication with the hollow tube, the securing mechanism adapted to receive and lock the instrument in place while also providing for at least some adjustment of the instrument such that the instrument can be adjusted to protrude from the distal end, be flush with the distal end, be retracted from the distal end into the hollow tube, and combinations thereof, while the instrument remains locked in place; and (d) an adapter for changing the working length of the hollow tube allowing the cannula device to be used for both small and large joints.

21. The small diameter cannula device of claim 20, wherein the adapter is adapted to protrude from the end of the main body from which the hollow tube protrudes for shortening the insertable portion of the hollow tube and for adapting the cannula device for use with small joints.

22. A method for performing an office-based diagnostic procedure, comprising:

(a) providing at least one small diameter cannula device, the at least one cannula device comprising:
   (i) a hollow tube adapted to receive a fiberoptic scope and having a distal end sized for insertion into a patient for diagnosis or treatment during an office-based procedure;
   (ii) a main body having an end from which the hollow tube protrudes; and
   (iii) a securing mechanism at the other end of the main body and in communication with the hollow tube, the securing mechanism adapted to receive and lock a fiberoptic scope in place while also providing for at least some adjustment of the scope such that the scope can be adjusted to protrude from the distal end, be flush with the distal end, be retracted from the distal end into the hollow tube, and combinations thereof, while the scope remains locked in place;
(b) creating an entry path in order to deliver the cannula device to the desired surgical site;
(c) inserting the cannula device through the entry path;
(d) inserting a fiberoptic scope and securing the scope in place with the securing mechanism; and
(e) viewing the site.

23. The method of claim 22, wherein the (b) creating an entry path in order to deliver the cannula device to the desired surgical site and (c) inserting the cannula device through the entry path, comprise:
   (i) placing a needle through a patient's skin in order to form an entry path to the surgical space;
   (ii) removing the needle from the patient;
   (iii) inserting a trocar into the cannula;
   (iv) inserting the trocar and cannula through the entry path created by the needle to a point near the desired surgical site;
   (v) removing the trocar;
   (vi) inserting an obturator into the cannula;
   (vii) advancing the obturator and cannula to the surgical site, whereby the use of the obturator is adapted to minimize potential damage to tissue; and
   (viii) removing the obturator.

24. The method of claim 23, wherein the surgical site is a synovial joint, and the (vii) advancing the obturator and cannula to the surgical site comprises advancing the obturator and cannula down to the joint capsule.

25. The method of claim 22, wherein the (b) creating an entry path in order to deliver the cannula device to the desired surgical site and (c) inserting the cannula device through the entry path, comprise:
   (i) placing a needle through a patient's skin in order to form an entry path to the surgical space;
   (ii) removing the needle from the patient;
   (iii) forming a small incision at the surface of the patient's skin sized to accommodate the cannula device;
   (iii) inserting an obturator into the cannula device;
   (vii) advancing the obturator and cannula to the surgical site, whereby the use of the obturator is adapted to minimize potential damage to tissue; and
   (viii) removing the obturator.

26. The method of claim 25, wherein the surgical site is a synovial joint, and the (vii) advancing the obturator and cannula to the surgical site comprises advancing the obturator and cannula down to the joint capsule.

27. The method of claim 22, further comprising:
   (f) applying an irrigation or suction tube to the connection port in order to irrigate or suction the site.

28. The method of claim 22, wherein a therapeutic treatment is delivered through the hollow tube.

29. The method of claim 22, wherein the (a) providing a small diameter cannula device further comprises:
   attaching an adapter to an end of the main body to shorten the insertable portion of the hollow tube and for adapting the cannula device for use with small joints.

30. A kit for performing a diagnostic procedure, comprising:

(a) at least one small diameter cannula device, comprising:
   (i) a hollow tube adapted to receive a fiberoptic scope and having a distal end sized for insertion into a patient for diagnosis or treatment during an office-based procedure;
   (ii) a main body having an end from which the hollow tube protrudes; and
   (iii) a securing mechanism at the other end of the main body and in communication with the hollow tube, the securing mechanism adapted to receive and lock a fiberoptic scope in place while also providing for at least some adjustment of the scope such that the scope can be adjusted to protrude from the distal end, be flush with the distal end, be retracted from the distal end into the hollow tube, and combinations thereof, while the scope remains locked in place;
(b) an adapter for changing the working length of the hollow tube allowing the cannula device to be used for both small and large joints;
(c) a fiberoptic scope; and
(d) a trocar, a blunt obturator, or both, to assist entry of the cannula into a patient.

31. The kit of claim 30, further comprising one or more of tubing for connection to irrigation or suction sources, bandages for application to the wound site, gauze pads, alcohol swabs, surgical drapes, or any combination thereof.

32. A small diameter cannula device, comprising:
(a) a hollow tube adapted to receive a fiberoptic scope, the tube having a distal end sized for insertion into a patient for diagnosis or treatment during an office-based procedure;
(b) a main body having an end from which the hollow tube protrudes; and
(c) a securing mechanism, comprising
   (i) a core body with at least one alignment slot;
   (ii) an adapter body that fits at least partially within the core body and including at least one post adapted to fit in the at least one alignment slot and a j-hook slot adapted to receive a protrusion of the scope; and
   (iii) a rotatable collar with at least one adjustment slot adapted to receive the at least one post, wherein the rotatable collar fits over the core body and the adapter body.

* * * * *